(12) United States Patent
Bojanowski et al.

(10) Patent No.: US 9,238,153 B2
(45) Date of Patent: Jan. 19, 2016

(54) TRANSORAL METHODS AND COMPOSITIONS FOR WRINKLE REDUCTION AND COSMETIC LIP AND FACIAL AUGMENTATION

(75) Inventors: Krzysztof Bojanowski, Santa Paula, CA (US); Hui Zhao, Santa Paula, CA (US)

(73) Assignee: Sunny BioDiscovery, Inc., Santa Paula, CA (US)

( * ) Notice: Subject to any disclaimer, the term of this patent is extended or adjusted under 35 U.S.C. 154(b) by 0 days.

(21) Appl. No.: 14/112,471

(22) PCT Filed: Apr. 20, 2012

(86) PCT No.: PCT/US2012/034424
§ 371 (c)(1),
(2), (4) Date: Nov. 15, 2013

(87) PCT Pub. No.: WO2012/145609
PCT Pub. Date: Oct. 26, 2012

(65) Prior Publication Data
US 2014/0301958 A1    Oct. 9, 2014

Related U.S. Application Data

(60) Provisional application No. 61/477,942, filed on Apr. 21, 2011.

(51) Int. Cl.
| | | |
|---|---|---|
| *A01N 65/00* | (2009.01) | |
| *A61Q 1/00* | (2006.01) | |
| *A61K 8/44* | (2006.01) | |
| *A61K 8/49* | (2006.01) | |
| *A61K 8/55* | (2006.01) | |
| *A61K 8/67* | (2006.01) | |
| *A61K 8/73* | (2006.01) | |
| *A61Q 19/08* | (2006.01) | |
| *A61K 8/92* | (2006.01) | |
| *A61K 8/97* | (2006.01) | |
| *A61K 8/02* | (2006.01) | |

(52) U.S. Cl.
CPC ................ *A61Q 1/00* (2013.01); *A61K 8/0208* (2013.01); *A61K 8/44* (2013.01); *A61K 8/4913* (2013.01); *A61K 8/4926* (2013.01); *A61K 8/553* (2013.01); *A61K 8/671* (2013.01); *A61K 8/731* (2013.01); *A61K 8/922* (2013.01); *A61K 8/97* (2013.01); *A61Q 19/08* (2013.01); *A61K 2800/92* (2013.01)

(58) Field of Classification Search
CPC ...................................................... A61K 36/00
USPC ...................................................... 424/725
See application file for complete search history.

(56) References Cited

U.S. PATENT DOCUMENTS

| | | |
|---|---|---|
| 5,571,533 A | 11/1996 | Santus et al. |
| 6,224,850 B1 | 5/2001 | Breton et al. |
| 6,620,419 B1 | 9/2003 | Lintner |
| 7,906,140 B2 | 3/2011 | Bromley et al. |
| 8,252,323 B2 | 8/2012 | Bromley et al. |
| 8,414,914 B2 | 4/2013 | Bromley et al. |
| 2004/0126352 A1 | 7/2004 | Jones |
| 2004/0192598 A1 | 9/2004 | Kragie |
| 2005/0025737 A1 | 2/2005 | Sebagh |
| 2009/0068255 A1 | 3/2009 | Yu et al. |
| 2010/0055138 A1 | 3/2010 | Margulies et al. |
| 2010/0080829 A1 | 4/2010 | Dulieu et al. |

FOREIGN PATENT DOCUMENTS

EP          2046283 B1     3/2011

OTHER PUBLICATIONS

Akazawa, Y., et al., "Adiponectin Resides in Mouse Skin and Upregulates Hyaluronan Synthesis in Dermal Fibroblasts", Connect. Tissue Res., pp. 322-328, 2011.
Babish, J.G., et al., "Antidiabetic Screening of Commercial Botanical Products in 3T3-L1 Adipocytes and db/db Mice", J. Med. Food, vol. 13, p. 535, 2010.
Coleman, S., et al., "A Comparison of Lipoatrophy and Aging: Volume Deficits in the Face", Aesthetic Plastic Surgery, vol. 33, pp. 14-21, 2009.
Dixit, R.P., et al., "Oral Strip Technology: Overview and Future Potential", Journal of Controlled Release, vol. 139, p. 94-107, 2009.
Du, Y., et al., "Adipose-derived stem cells differentiate to keratocytes", Mol. Vis., vol. 16, pp. 2680-2689, 2010.
Fernandes, C., et al., "Blepharoplasty Gets a Lift", Plastic Surgery Practice, Jan. 2011, (www.plasticsurgerypractice.com/issues/articles/2011-01__03.asp).
Gierloff, M., et al., "Aging Changes of the Midfacial Fat Compartments: A Computed Tomographic Study", Plastic & Reconstructive Surgery, vol. 129, p. 263, 2012.
Rajurkar, N.S., et al., "Estimation of phytochemical content and antioxidant activity of some selected traditional Indian medicinal plants", Indian J. Pharm. Sci., vol. 73, Issue 2, pp. 146-151.
Shojaei, A.H., "Buccal Mucosa as a Route for Systemic Drug Delivery: A Review", J. Pharm. Pharmaceut. Sci., vol. 1, Issue 1, pp. 15-30, 1998.
Song, F.L., et al., "Total Phenolic Contents and Antioxidant Capacities of Selected Chinese Medicinal Plants", Int. J. Mol. Sci., vol. 11, p. 2362-2372, 2010.

*Primary Examiner* — Michael Meller
(74) *Attorney, Agent, or Firm* — Taft Stettinus & Hollister LLP

(57) ABSTRACT

The purpose of this patent is to teach the methods of application and compositions of cosmetic and therapeutic products for reducing wrinkle appearance and augmenting certain compartments of the facial integument of a mammal, especially a human. These methods and compositions utilize the hypodermis-targeted release from bioadhesive oral films, pastes or patches applied to oral mucosa or teeth for the purpose of improving the appearance or health of the lips and facial skin.

19 Claims, No Drawings

TRANSORAL METHODS AND COMPOSITIONS FOR WRINKLE REDUCTION AND COSMETIC LIP AND FACIAL AUGMENTATION

CROSS-REFERENCES TO RELATED APPLICATIONS

This application claims priority to provisional U.S. Patent Application Ser. No. 61/477,942, filed Apr. 21, 2011, the contents of which are incorporated herein by reference in their entirety.

BACKGROUND OF THE INVENTION

Skin is our largest organ and the one that ages the most conspicuously—especially in the facial region. Often, a person's facial appearance determines the viewer's perception of that person's age.

A major area of focus for the cosmetic industry is the improvement of facial appearance. This improvement can be understood to relate to both the protection of the skin, to prevent damage caused by environmental conditions, and also to rejuvenation of the skin, to ameliorate damage which has occurred. Skin rejuvenation products are often referred to as "anti-aging" products.

While skin protection products are well known, such as topical sunblocks and moisturizers, effective skin rejuvenation or anti-aging products are not so common, and such existing products present room for improvement. Accordingly, there remains a need for safe and effective skin rejuvenation or anti-aging products and improved methods for their delivery.

One reason that the need for skin rejuvenation or anti-aging products remains unfulfilled may be that the current prevailing approach used in the cosmetic industry is naïve, consisting in applying selected active ingredients onto the epiderm, a protective barrier which specifically functions to prevent penetration and seal off the organism from the outside world. Further, even if the active ingredient is able to penetrate the epidermal barrier and reach the level of the dermal-epidermal junction, it has still only reached the very surface of the problem area. This is because in great part, skin aging is the consequence of processes unfolding in the most internal part of the integumentary system, the hypodermis, which is also known as the hypoderm, subcutaneous tissue, or superficial fascia. Here, "integumentary" means cutaneous, while "integument" means "skin and its derivatives." The hypodermis is the lowermost layer of the integumentary system, which, for the face is composed of fibrous bands anchoring the skin to the deep fascia, fat, blood vessels, lymphatic vessels, hair follicle roots, sudiferous gland structures, nerves and facial expression (panniculus carnosus) muscles. The hypodermal adipose tissue nurses and nourishes the dermal and the epidermal layers of the skin, facial expression muscles respond to nerve stimuli by contracting and folding the dermal tissue, and blood vessels supply oxygen and evacuate the metabolic waste.

In summary, skin health and appearance is greatly determined by the condition of its innermost component, the hypodermis.

Facial aging can be characterized by a progressive thinning of the hypoderm, including fat loss or lipoatrophy, resulting, among other morphological effects in substantial collapse of the facial volume especially at the level of the medial cheeks, also known as face hollowing. See, e.g., Gierloff, M., Stöhring, C., Buder, T., Gassling, V., Açil, Y., Wiltfang, J., Aging Changes of the Midfacial Fat Compartments: A Computed Tomographic Study, *Plastic & Reconstructive Surgery*, 2012; 129: 263. In extreme cases, such as in some AIDS treatments, lipoatrophy can progress toward nearly complete subdermal facial fat loss. See, e.g., Coleman, S., Saboeiro, A. and Sengelmann, R., A Comparison of Lipoatrophy and Aging: Volume Deficits in the Face. Aesthetic, *Plastic Surgery*, 2009; 33, 14. The regression of hypodermis contributes not only to face hollowing and skin thinning, but also to wrinkles, because the skin loses its source of nutrition and regeneration, while being continuously subjected to fold-unfold cycles through the action of the facial expression muscles. Accordingly, some plastic surgery rejuvenation techniques involve the use of grafts of fat tissue. See, e.g., Fernandes, D, and Kaplan, H., Blepharoplasty Gets a Lift. *Plastic Surgery Practice*, January 2011 (www.plasticsurgerypractice.com/issues/articles/2011-01_03.asp).

Similarly, ageing can be characterized by an overall muscle loss or sarcopenia. In that regard, facial muscle mass augmentation can be desirable in order to maintain a youthful facial appearance. The term "augmentation" as used in the present invention relates to increase in the volume of soft tissue.

The delivery of suitable active cosmetic ingredients by topical application onto the epidermis, with or without iontophoresis or electroporation, and also by subcutaneous or intradermal injections is known in the art. Another known method of delivery of skin-beneficial cosmetics is via oral delivery, i.e., by ingestion. For example, U.S. Pat. No. 6,224,850 discloses examples of several routes of known cosmetic product applications. However, none of prior art of which we are aware addresses the benefits of intraoral application of cosmetics through a transmucosal route for direct interaction specifically with the hypoderm, and resulting in benefits including: decrease in the unattractive visibility of gums while smiling or laughing known as "gummy smile" through hypodermal muscle relaxation in the parafiltrum (skin between the nose and the upper lip); lip plumping through the vasodilatation of hypodermal vessels, swelling or sensory stimuli; cheek plumping through the support and augmentation (increase in volume) of the hypodermal adipose tissue and hypodermal muscles; smoother skin appearance through regenerative action on the hypodermis supporting hair follicles and their muscles; prevention of skin drying through the regenerative effect on hypodermal sebaceous glands; and improved appearance of facial wrinkles through hypodermal muscle relaxation, hypodermal adipose tissue augmentation or stimulation of adipokines, which support the extracellular matrix and basement membrane components of the skin.

SUMMARY OF THE INVENTION

Provided herein are compositions and methods for providing cosmetic benefit to the facial skin of an animal, including a human. Provided are compositions and methods for the delivery of cosmetic ingredients to the facial integument of an animal, including a human, employing intraorally-applied bioadhesive vehicles that facilitate delivery of selected cosmetic compounds through a transmucosal route for interaction specifically with the facial hypoderm. The compositions and methods provided herein may provide benefits including, inter alia, a decrease in gummy smile appearance through hypodermal muscle relaxation in the parafiltrum; lip plumping through the vasodilatation of hypodermal vessels, sensory effect on hypodermal nerve endings, hypodermal muscle relaxation or intraintegumental swelling; cheek plumping through support or augmentation of hypodermal adipose tissue and hypodermal muscles; smoother skin appearance through regenerative action on the hypodermis supporting hair follicles and their muscles; prevention of skin drying through the regenerative effect on hypodermal sebaceous glands and improved appearance of facial wrinkles through hypodermal muscle relaxation, hypodermal adipose tissue augmentation or beneficial regulation of adipokines (cytokines secreted by adipocytes), having for effect regeneration of the integumental components.

The compositions and methods disclosed herein provide efficient delivery of cosmetic compounds via intraorally-applied, hypodermis-targeted bioadhesive delivery systems, which allow the cosmetic compounds to reach the hypodermal tissue, which otherwise is out of reach for topically-applied products. Without being bound by scientific theory, it is believed that the hypodermal tissue nourishes/nurses, shapes and supports facial skin physically, through the vasculature, muscles and through the secretion of adipokines, such as adiponectin, which has been recently reported to have beneficial effects on wound healing and on the skin structure in general, such as upregulation of hyaluronan synthesis by dermal fibroblasts. See, e.g., Akazawa, Y., Sayo, T., Sugiyama, Y., Sato, T., Akimoto, N., Ito, A., and Inoue, S., Adiponectin Resides in Mouse Skin and Upregulates Hyaluronan Synthesis in Dermal Fibroblasts, *Connect. Tissue Res.*, 2010; 30.

Without being bound by scientific theory, it is believed that the cosmetic compounds delivered via the compositions and methods disclosed herein can stimulate adipocytes to increase absorption of free fatty acids and thus decrease lipotoxicity, increase the preadipocyte differentiation, and thus prevent or retard atrophy of the hypodermis, or stimulate the differentiation of progenitor cells in the hypodermal tissue to adipocytes, fibroblasts, keratinocytes or muscle fibers and thus improve the function, structure and thickness of this tissue, which is known to get thinner with age. See, e.g., Du, Y., Roh, D. S., Funderburgh, M. L., Mann, M. M., Marra, K. G., Rubin, J. P., Li, X., and Funderburgh, J. L., Adipose-derived stem cells differentiate to keratocytes, *Mol. Vis.*, 2010; 16: 2680.

Without being bound by scientific theory, it is believed that, in certain embodiments, the cosmetic compounds delivered to the hypodermis via the compositions and methods disclosed herein can act on facial expression muscles, and, for example relax those muscles. This relaxation of the facial muscles is believed to decrease the visible appearance of facial wrinkles around the circumferential vermilion-skin border and decrease the appearance of gummy smile.

In another embodiment, the compositions provided herein are formulated to contact the oral mucosal membrane or teeth of an animal, including a human, for a period of time from 1 minute up to 24 hours. If the desired effect is instant lip plumping, the oral strip carrier should degrade and deliver the cosmetic active ingredient within not more than about 60 minutes. If the desired effects are not instantaneous, such as in the case of gummy smile reduction, cheek augmentation or wrinkle reduction, the product can be applied to the mucosal tissue or teeth at or prior to the subject going to bed, and the release of the active cosmetic compound should be effected over a period of between about 1 and about 8 hours. The compositions provided herein can have a wide range of viscosities, because compositions having viscosities in the range from as low as about 200 to 1000 cps up to viscosities in the range of about 500,000 cps can achieve satisfactory bioadhesion.

The compositions of the present invention may take any suitable physical form, but are preferably bioadhesive oral slow release films, pastes, or powders.

The compositions provided herein are formulated to remain stable over a relatively long period of time. For example, the compositions provided herein are preferably stored at room temperature, and preferably remain stable for at least 1 day, 1 week, 1 month, or, in certain embodiments up to more than 1 year. The most preferred compositions are stable for more than 1 year.

The above-mentioned systems can be paired with a topical cosmetic product for additional or enhanced skin-beneficial activity, including protection.

In one embodiment, the present invention provides compositions for providing cosmetic benefit to the facial skin of an animal, wherein said composition comprises a bioadhesive vehicle and at least one cosmetic and/or therapeutic compound, and wherein said composition is applied to the patient intraorally. In another embodiment, the present invention provides methods for intraoral transmucosal delivery of a cosmetic or therapeutic compound, comprising contacting the intraoral mucosa of an animal with one or more of the compositions of the invention, whereby the cosmetic or therapeutic compound is targeted for delivery to the hyperdermal tissue of the patient. The cosmetic benefits provided by the compositions and methods of the present invention include reduction in appearance of wrinkles in the facial skin and cosmetic augmentation in the facial integument, wherein the cosmetic augmentation in the facial integument may include altering or improving the appearance of at least one of the following: thin lips, gummy smile, dry lips, dry skin, lines, depressed hair follicles, and/or wrinkles on and around lips, hollow cheeks, collapsed cheeks, and sagging skin in and around the jaw area.

In one embodiment of the present invention the cosmetic or therapeutic compound is a compound having high lipogenic activity, a compound which causes muscle relaxation, a compound which causes lip-plumping, a compound which causes lip and facial skin augmentation via improvement of the extracellular matrix by stimulation of glycoaminoglycans, collagens and elastin or a compound which causes plumping of the facial integument. Preferably the compositions comprise from about 5% to about 20% of the cosmetic or therapeutic compounds which cause muscle relaxation or which have high lipogenic activity.

In another embodiment, the cosmetic or therapeutic compound which causes plumping of the facial integument is a compound which stimulates lipogenesis or inhibits lipolysis.

In another embodiment the compositions of the present invention may be applied to an animal, preferably a human, intraorally under labiomental skin, under parafiltrum, on cheek mucosa, on teeth or on gums.

In another embodiment the compositions of the present invention comprise a combination of extracts from *Vitis vinifera* seed and *Portulaca oleracea* above-ground parts, a phospholipid, pectin and an ascorbic acid derivative.

In another embodiment the cosmetic or therapeutic compound which causes muscle relaxation is γ-aminobutyric acid, or an extract from a plant belonging to the family of Asteraceae, Portulacaceae or Iridaceae. A preferred compound of the Portulacaceae family is *Portulaca oleracea* aqueous extract.

In one embodiment, the compositions of the present invention are applied onto the oral mucosa of the parafiltrum or upper jaw front teeth or upper jaw facial side of the gums for the purpose of causing increased lip coverage of upper gums and decrease of gummy smile through upper lip muscle relaxation or are applied onto the oral mucosa of the parafiltrum, labiomental skin, front teeth or facial side of the gums for the purpose of achieving reduced perioral wrinkle appearance through perioral muscle relaxation.

In another embodiment, the compositions may further comprise additional active materials, including, but not limited to, oral hygiene compounds, teeth whitening compounds, sialogogic compounds, and topical cream and lotion components.

In another embodiment, the compositions of the present invention may take the form of a patch, a film, an emulsion, a powder or a gel.

In one embodiment the composition of the present invention is a controlled release bioadhesive patch which comprises from about 1% to about 35% *Portulaca oleracea* (purslane) extract, from about 1% to about 35% grape seed extract, from about 2% to about 60% lecithin, and from about 0.1% to about 10% magnesium ascorbyl phosphate, and more preferably comprises from about 5% to about 15% purslane extract, from about 2% to about 10% grape seed extract, from about 5% to about 15% lecithin, and from about 0.2% to about 2% magnesium ascorbyl phosphate.

In one embodiment the composition of the present invention is a biodegradable bioadhesive patch which comprises from about 0.1% to about 10% niacin, from about 2% to about 20% proline, from about 0.1% to about 10% GABA, from about 0.01% to about 5% *Capsicum oleoresin*, from about 0.01% to about 2% menthol, and from about 0.1% to about 10% betaine, and more preferably comprises from about 0.2% to about 1% niacin, from about 5% to about 10% proline, from about 0.5% to about 2% GABA, from about 0.1% to about 0.5% *Capsicum oleoresin*, from about 0.1% to about 0.5% menthol, and from about 2% to about 6% betaine.

In one embodiment, the present invention provides methods for intraoral transmucosal delivery of a cosmetic or therapeutic compound, wherein the composition contacts the intraoral mucosal lining of an animal for a time sufficient to deliver an effective amount of the cosmetic compound to the hypodermal tissue. In another embodiment, the composition contacts the intraoral mucosal lining of an animal for a period of from about 1 minute to about 24 hours. In another embodiment, the composition contacts the intraoral mucosal lining of an animal for a period of from about 1 hour to about 8 hours. In yet another embodiment, the composition contacts the intraoral mucosal lining of an animal for a period of up to about 1 hour.

In another embodiment the present invention provides methods for intraoral transmucosal delivery of a cosmetic or therapeutic compound, wherein the composition provides a cosmetic augmentation in the facial integument which comprises altering or improving the appearance of at least one of the following: thin lips, gummy smile, dry lips, dry skin, lines, depressed hair follicles and/or wrinkles on and around lips, hollow cheeks, collapsed cheeks, and sagging skin in and around the jaw area.

DETAILED DESCRIPTION OF THE INVENTION

Repetitive contraction of facial expression integumental muscles over the lifetime of an animal, especially a human, coupled with the progressive loss of the hypodermis mass and function, greatly contribute to the development of wrinkles, while the collapse of facial hair follicles and surrounding cell structures leads to the development of depressed hair follicles in the skin. In addition, loss of fat and muscle mass with aging can contribute to face hollowing and sagging, and decreased activity of sebaceous glands to suboptimal protection of skin from drying. The present invention provides compositions and methods for providing cosmetic benefit to the facial skin of an animal, including a human. The compositions and methods of the present invention provide intraoral delivery of cosmetic compounds, including, for example, muscle-relaxing, vasodilating, sensory, and hypodermis-supporting cosmetic materials, by formulating such cosmetic compounds in an intraoral bioadhesive vehicle. The compositions and methods of the present invention provide sensory benefits such as a feeling of fuller lips, and also support and nourish the facial integument, and relax facial expression muscles, including panniculus carnosus muscles, resulting in attenuation of the appearance of wrinkles or depressed hair follicles.

In another embodiment, the compositions and methods of present invention provide relaxation of integumental muscles resulting in an elongation of the parafiltrum, and a reduction of the appearance of "gummy smile," a condition wherein a subject's smile, especially a human's smile, unwillingly uncovers the gums. The "gummy smile" is often considered unattractive and is currently treated with surgery or Botox injections. Accordingly, a need remains for a non-invasive self-applied cosmetic treatment to ameliorate the appearance of the "gummy smile."

Methods and Compositions

The present invention provides compositions and methods for providing cosmetic benefit to the facial skin of a mammal, including a human, by delivery of selected cosmetic compounds to the hypodermis via intraoral transmucosal delivery from a bioadhesive vehicle. The bioadhesive transoral delivery platform, which may be layered (for example composed of a hydrophilic layer superposed on a hydrophobic layer, or vice versa, or a system of multiples of such layers each capable of containing cosmetic materials with different physicochemical properties) or non-layered, contains cosmetic and/or therapeutic active compounds, including, but not limited to, vitamins and their derivatives; lipids; phospholipids; proteins; peptides; minerals; protein hydrolysates; amino acid derivatives; polyphenols; isoflavonoids; flavonoids; natural phenols; chalconoids; disulfides; thiols; phenylethanoid and caffeic acid sugar esters; steroids; stilbenes; glycosides; peptidoglycans, disaccharides, oligosaccharides, polysaccharides, terpenes; meroterpenes; indole alkaloids and their esters; carotenoids; xanthones; betaines; nucleic acids; extracts from plants; algae; mushrooms; yeast; plankton; bacterial or other microbial sources; peats; in vitro plant cell cultures; mushroom cell cultures and plant stem cells.

The compositions and methods of the invention provide one or more of the following benefits: lip-plumping; cheek-plumping; wrinkle-reducing; skin-smoothing; and reduction in appearance of gummy smile.

In certain embodiments, the compositions and methods of the invention provide delivery of suitable cosmetic and/or therapeutic compounds to the hypodermis through the transoral mucoadhesive delivery to provide the benefit of amelioration and/or treatment of detoxification; soothing; wound healing; anti-rosacea; anti-itching; anti-psoriatic; anti-rash; and/or anti-acne activities for the skin.

Without being bound by scientific theory, it is believed that the skin-beneficial activity of cosmetic and/or therapeutic compounds transorally delivered from the bioadhesive vehicles of the invention may be due to lipogenic; adiponectin-stimulatory; anti-lipolytic, anti-lipodystrophic; muscle-relaxant; anti-lipotoxic; anti-advanced glycation end product (AGE) formation; glucose-normalizing; adipokine-modulatory; leptin-modulatory; peroxisome proliferator-activated receptor (PPAR)-gamma-stimulatory; sterol regulatory element-binding transcription factor 1 (SREBP-1)-stimulatory; hypolipidemic; collagen-stimulatory; ECM-stimulatory; matrix metalloproteinase-inhibitory; anti-lipolytic; anti-oxidant; glycosaminoglycan-stimulatory; swelling-inducing; sensory; or anti-inflammatory activity. It is further believed that the compositions of the invention may promote stem cell differentiation into muscle fibers;—fibroblasts; keratinocytes; or adipocytes.

Compounds with above-mentioned cosmetic or therapeutic activities have been described in the past and are well known by persons skilled in the art, but not in connection with orally-applied bioadhesive vehicles that facilitate delivery of selected cosmetic compounds through a transmucosal route for direct interaction specifically with the hypoderm. For example, examples of anti-inflammatory, PPAR-, lipogenesis- and adiponectin-stimulatory botanical extracts are described in Babish, J. G., Pacioretty, L. M., Bland, J. S., Minich, D. M., Hu, J., and Tripp, M. L., Antidiabetic Screening of Commercial Botanical Products in 3T3-L1 Adipocytes and db/db Mice, *J. Med. Food,* 2010; 13: 535. The disclosed extracts having high lipogenic activity would be suitable for transoral delivery in the orally-applied bioadhesive vehicles of the present invention. For the purpose of this invention, "high lipogenic activity" of a cosmetic active is defined as an ability to achieve a lipogenic index (LI) of 1.5 or higher, as defined by Babish, et al., *J. Med. Food,* 2010; 13: 535.

Suitable anti-inflammatory compounds may be lipoxygenase (LOX)-, cyclooxygenase (COX)-, metalloproteinase-inhibitory or may have another known anti-inflammatory mechanism of action. Mixtures of two or more anti-inflammatory compositions, especially those with different mechanisms of action, may be more beneficial than corresponding equal weight amounts of one single ingredient. Examples of suitable anti-inflammatory compounds include, but are not limited to COX inhibitors, including eugenol, cardamonin, plant extracts including ginger root and *Zingiber officinalis* root, *Scutellaria baicalensis*, Clove family, *Syzygium aromaticum, Eucomis, Celastrus, Celastrus orbiculatus, Evodia rutaecarpa* fruit, *Kochia, Kochia Scoparia, Notopterygium incisum, Syzygium cumini, Alpinia* species and the like; LOX-5 inhibitors, including extracts from *Alpinia officinarum, Boswellia serrata, Notopterygium incisum* and the like; superoxide inhibitors, including turmeric, *Curcuma longa* root extract and the like; cytokine inhibitors, including luteolin, spilanthol, Bettie nut, *Tithonia* or *Tithonia diversifolia*, tea polyphenols and the like, nitric oxide signaling pathway inhibitors, including Coptis, Cinnamon, *Cinnamonum cassia*, Mexican bamboo, *Polygonum cuspidatum* and the like; and compounds with multiple mechanisms of action, such as *Psoralea, Rumex, Baccharis*, Feverfew, *Vitis vinifera* seed, Mango Ginger, or *Curcuma amada, Stephania*, and *Corydalis*, or *Corydalis Turtschaminovii* root extract, horse chestnut extract (*Aesculus hippocastanum* extract), esculin, escin, yohimbine, *capsicum oleoresin*, capsaicin, niacin, niacin esters, methyl nicotinate, benzyl nicotinate, ruscogenins (butchers broom extract; *Ruscus aculeatus* extract), diosgenin (*Trigonella foenumgraecum*, fenugreek), *Phyllanthus emblica* extract, asiaticoside (*Centella asiatica* extract), piperine, vitamin K, melilot (*Melilotus officinalis* extract), glycyrrhetinic acid, Ursolic acid, sericoside (*Terminalia sericea* extract), darutoside (*Siegesbeckia orientalis* extract), *Amni visnaga* extracts, *Myrtus communis* extracts, *Portulaca oleracea* extracts, apigenin, phytosan, bakuchiol and luteolin. Without being bound by scientific theory, because the generation of free radicals is an inherent part of the immune response, many antioxidants mentioned in the paragraph below have also anti-inflammatory properties and can be used as such in this invention.

Examples of antioxidant plant extracts are disclosed in e.g., Song, F. L., Gan, R. Y, Zhang, Y., Xiao, Q., Kuang, L. and Li, H. B., Total Phenolic Contents and Antioxidant Capacities of Selected Chinese Medicinal Plants, *Int. J. Mol. Sci.,* 2010, 11, 2362; and Rajurkar, N. S, and Hande, S. M., Estimation of phytochemical content and antioxidant activity of some selected traditional Indian medicinal plants, *Indian J. Pharm. Sci.,* 2011, 73(2):146. Examples of suitable anti-oxidant compounds include peptidoglycans, such as Lycium barbarum peptidoglycans; polyphenols, including oleuropein, tea polyphenols and the like; flavonoids, including quercetin, corsitin, luteolin, diosmin and the like; their glycosides, including rutin, hesperidin and the like; anthocyanidins, including cyanidin and the like; proanthocyanidins, including oligomeric proanthocyanidins found in grape seeds and pine bark and the like; natural phenols, including rosmarinic acid, ellagic acid, resveratrol, tetrahydrocurcumin, curcumin and the like; xanthones, including mangiferin, mangostin and the like; carotenoids, including staxanthin, lycopene, carotene, retinol and retinoic acid, xanthophyll and the like; anthraquinones, including hypericin and the like; organosulfur compounds, including lipoic acid, cystein, N-acetyl-cysteine and the like; isoflavones, including genistein and the like; caffeic acid esters, including chlorogenic acid, verbascoside and the like; steroid glycosides, including ginsenosides and the like; stilbenes, including resveratrol and the like; tocopherols; tocotrienols; vitamin B compounds, including niacin, niacinamide and the like; meroterpenes, including bakuchiol and the like; ascorbic acid and derivatives thereof, including magnesium ascorbyl phosphate; and plant or fruit extracts, including pomegranate fruit extract, blueberry fruit polyphenolic extracts, coffee and coffeeberry extracts and the like.

In certain embodiments, the desired effect of facial plumping may be obtained through muscle augmentation by transmucosal delivery of cosmetic actives to hypodermis. Without being bound by scientific theory, it is believed that muscle augmentation effect may be due to either the inhibition of muscle waste (sarcopenia), or stimulation of myocyte differentiation into mature muscle fiber, or a combination thereof. Examples of suitable muscle-augmenting compounds, include, but are not limited to ornithine, ornithine alpha-ketoglutarate, leucine, arginine, beta-hydroxy-beta-methyl-butyrate (bHMB), creatine, creatine monohydrate, creatine phosphate, creatine pyruvate, creatine ascorbate and the like. Antioxidant protection of muscles by antioxidant and anti-inflammatory compounds, extracts and isolates mentioned above can also slow muscle wasting, and such compounds would be suitable for use in the transorally-delivered bioadhesive compositions of the present invention.

Compounds having the effect of causing relaxation of muscles are suitable for use in the transorally-delivered bioadhesive compositions of the present invention. In particular, muscle relaxation is desirable in bringing about effects such as reduction in appearance of gummy smile, and peri-oral wrinkle reduction. Examples of suitable muscle-relaxant actives, which can be delivered to the hypodermis through oral bioadhesive transmucosal method of delivery discussed in this disclosure include, but are not limited to the following: 1) compounds which antagonize acetylcholine-mediated signal transduction pathways, such as berberine, Argemone ochroleuca extracts, toosendanin and azadirachtin and the like, certain SNARE-interfering peptides such as acetyl hexapeptide-3 (with or without a palmityl or myristyl tail) and the like, and dipeptide diaminobutyroyl benzalamide diacetate; 2) compounds which interact with GABA receptors, such as γ-Aminobutyric acid and extracts from Iridaceae family of plants and the like; 3) calcium channel inhibitors, such as soy protein extracts and phytoestrogens Genistein, phloretin and biochanin A, phenylalkylamines, dihydropyridines, benzothiazepines, diphenylpiperazine, verapamil, anipamil, gallopamil, devapamil, falipamil, tiapamil, nifedipine, amlodipine, dazodipine, felodipine, isradipine, lanicardipine, nimodipine, nisoldipine, nitrendipine, ryosidie, diltiazem, cinnarizine, and flunarizine, calmodulin antagonists, naphthalenes, and dopamine antagonists including dantrolene, TMB-8, phenothiazine, trifluoperazine, chlorpromazine, dibucaine, pimozide, haloperidol, calmidazolium and the like; 4) nicotinic receptor agonists; 5) compounds which interfere with nitric oxide-mediated signal transduction, such as luteolin, polyarginine, arginine, extracts and isolates from *Angelica sinensis*, and the like; 6) chlorine channel agonists; 7) extracts of the Portulacaceae family of plants and the like, including isolates from green parts of *Portulaca oleracea*, the muscle relaxant activity of which, without being bound by scientific theory, is believed to be due to anticholinergic, histamine H1 receptor-inhibitory, calcium homeostasis-regulatory or beta-adrenergic-stimulatory effect; 8) cannabinols and the like including extracts and isolates from cannabis; 9) other histamine H1 receptor-inhibitory compounds, theophylline and the like; 10) *Ligusticum wallichi* and *Angelica gigas* extracts and isolates and the like (the activity of which, without being bound by scientific theory, are believed to be through the inhibition of calcium flux to the muscle and the action on the potassium channel). Multicomponent botanical extracts causing muscle relaxation may have a complex mechanism of action, which cannot be assigned to one particular category. Such extracts include, but are not limited to *Hyssopus officinalis, Crocus sativus, Chelidonium majus, Piper methysticum, Perilla frutescens, Pheretima aspergilum, Himatanthus lancifolius, Aegle marmelos* Corr. Leaves, *Desmodium adscendens, Spondias mombin, Mentha piperita, Acmella oleracea, Portulaca oleracea* aerial parts, *Curcuma caesia, Gnaphalium liebmannii*, Criollo cocoa beans, *Artemisia vulgaris, Dichrostachys cinerea, Paeonia emodi*, Radix Aconiti lateralis, Licorice root and the like.

In certain embodiments, the desired effect of lip plumping may be obtained by oral transmucosal delivery of cosmetic actives to hypodermis. Without being bound by scientific theory, it is believed that lip plumping may be brought about by utilizing lipogenic, vasodilating, muscle-relaxing, swelling-inducing or sensory-enhancing actives. Examples of suitable lip plumping materials include, but are not limited to, botanical extracts and isolates from plants, including *Vitis vinifera* seeds, *Angelica sinensis* roots, *Portulaca oleracea* green parts, *Acmella oleracea* green parts, *Ginko bilboa* leaves, Bettie nut, *Z. piperitum, Z. simulans, Z. schinifolium*, Sichuan pepper, *Capsicum* fruit, ginger root, *Epimedium sagittatum*, peppermint, clove, Tephrosia Purpurea seeds, *Solanum nigrum, Solanum scabrum, Passiflora incarnate, Psittacanthus calyculatus, Sesamum radiatum* leaves, *Ginko balboa, Vinca minor*, Korean red ginseng mint, peppermint and the like; phospholipids, including lecithin, vinpocetine, vincamine, niacin, isoalpha acids, rho-isoalpha acids, tea leaf polyphenols, xanthinol, alpha-tocopheryl nicotinate, xanthinol nicotinate, methyl nicotinate, benzyl nicotinate, vitamin E Nicotinate, arginine, polyarginine, citrulline, betaine, hydroxyoligocarboxylic esters, hydroxydicarboxylic esters, hydroxytricarboxylic esters, xylose, resorcinol, niacin, citrulline, menthol, N-methyl carboxamid, capsaicin, *Capsicum oleoresin* and the like.

The Extracellular matrix (ECM) is an acellular component of the dermal layer of the skin. We have now found that contacting the hypodermal layer of the human skin with lipogenic and anti-inflammatory cosmetic actives can trigger an improvement in the expression level of ECM components and appearance in the upper, dermal and epidermal layers of the skin, which demonstrates the utility of targeting such cosmetic active compounds to the hypodermis through the oral transmucosal delivery. See, e.g., Example 5, below. The inclusion of ECM component (such as collagens, hyaluronate, other glycoaminoglycans or elastin) production enhancing compounds is thus of biological importance for skin regeneration. Likewise, compounds which inhibit or reverse deleterious ECM modifications, such as advanced glycation end products (AGE) are valuable from the skin anti-aging perspective. Suitable compounds include, but are not limited to carnosine, lipoic acid, astaxanthin, chebulic acid, extracts from *Salvia reuterana, Zingiber officinalis* and *Artemisia campestris* and the like. Suitable ECM production enhancing compounds include, but are not limited to hesperedin (*Citrus sinensis*), diosmin (*Citrus sinensis*), mangiferin (*Mangifera indica*), mangostin (*Garcinia mangostana*), cyanidin (*Vaccinium myrtillus*), astaxanthin (*Haematococcus algae*), lutein (*Tagetes patula*), lycopene (*Lycopersicum esculentum*), resveratrol (*Polygonum cuspidatum*), tetrahydrocurcumin (*Curcuma longa*), rosmarinic acid (*Rosmarinus officinalis*), hypericin (*Hypericum perforatum*), polyphenols (*Camelia sinensis*), ellagic acid (*Punica granatum*), chlorogenic acid (*Vaccinium vulgaris*), oleuropein (*Olea europaea*), andrographolide (*Andrographis paniculata*), extracts and isolates from *Potentilla erecta, Centella asiatica, Puerariae radix, Arctium* lappa fruit, *Echinacea* and *Vitis vinifera* seeds, pycnogenol (pine bark extract), glucosamine, N-acetyl-glucosamine, xylose, ribose, proline, hydrolyzed whey protein, hydrolyzed wheat protein, hydrolyzed silk protein, hydrolyzed fish protein, hydrolyzed oat protein, hydrolyzed rice protein, quercetin, ascorbic acid, its salts and its derivatives sodium ascorbyl phosphate, magnesium ascorbyl phosphate, glucosamine ascorbate, arginine ascorbate, lysine ascorbate, glutathione ascorbate, nicotinamide ascorbate, niacin ascorbate, magnesium ascorbyl phosphate, allantoin ascorbate, creatine ascorbate, chondroitin ascorbate, chitosan ascorbate, DNA ascorbate, carnosine ascorbate, ascorbyl glucoside, rutinchondroitin, polyhydroxy acids, alpha hydroxy acids and their esters, algae extracts, chitosan, niacinamide, niacinamide derivatives, copper nucleotides, zinc nucleotides, manganese nucleotides, glutathione, carnosine, vitamin A and its derivatives, coenzyme Q10, lipoic acid, niacinamide lipoate, dimethylamino ethanol, vitamin E and its derivatives, tocotrienol, rutin, carotenoids, such as retinol and its derivatives, copper glucoside, zinc glucoside, manganese glucoside, peptides, such as tetrapeptide-7, tetrapeptide-3, pentapeptide-4, tripeptide-5 pentapeptide-3 and tripeptide-3, with and without palmityl and myristyl tails, derivatives of pentapeptides, and the like. Additionally, U.S. Pat. No. 6,620, 419 discloses peptide formulas of the general sequence palmitoyl-lysyl-threonyl-lysyl-serine, and combinations thereof, which compounds are also suitable production enhancing compounds in the compositions and methods of the present invention.

In another embodiment of the present invention, the transorally-delivered bioadhesive compositions of the present invention may further comprise a blood vessel protecting agent (for example preventing hemorrhage), such as Vitamin K, niacin, rosmarinic acid, extracts from *Angelica sinensis, Argusia argentea, Ficus hispida* or *Salvia miltiorrhiza*, or combinations thereof.

In another embodiment of the present invention, the orally-applied bioadhesive compositions of the present invention may further comprise an orally-active agent for teeth whitening, prevention of halitosis, antimicrobial and/or sialogogic and/or ulcer healing or pro-oral hygiene property for enhanced activity range. Such orally-active agents may be either layered on top of the hypodermis-targeting cosmetic agents or mixed with them, in the same bioadhesive delivery vehicle. Inclusion of such orally-active agents in the orally-applied bioadhesive compositions of the present invention may enable the compositions to simultaneously address skin and dental problems.

The orally-applied bioadhesive compositions of the present invention comprise a vehicle to transorally deliver the cosmetic compounds to the facial hypodermis. The vehicle is typically a pharmaceutically acceptable carrier capable of conforming to a contacted surface and which is capable of maintaining the contact so as to facilitate the transmucosal delivery. Bioadhesive technologies, suitable for cosmetic transoral delivery have been developed and are known by those skilled in the art. See, e.g., Dixit, R. P. and Puthli, S. P., Oral Strip Technology: Overview and Future Potential, *Journal of Controlled Release,* 2009, 139, 94, Shojaei, A. H., Buccal Mucosa As A Route For Systemic Drug Delivery: A Review, *J. Pharm. Pharmaceut. Sci.,* 1998, 1(1):15. However, the use of such technologies for delivery of cosmetic actives to the hypodermis is not known in the art. The term "bioadhesive" as used herein means a substance, inorganic or organic, natural or synthetic, that is capable of surface attachment to the oral mucosa or teeth.

Bioadhesive controlled release systems can spatially target and quantitatively improve the delivery of a selected active ingredient by extending the time of release of that compound and enhancing the exposure of the mucosa or other contacted surface to it. This is particularly important for actives which have limited bioavailability.

Suitable adhesive carriers for the transorally-delivered bioadhesive compositions of the present invention include any nontoxic polymers, particularly those which are water-soluble and of the type used for controlled drug delivery, meaning reproducibly released in a defined amount of time. Suitable such polymers include, but are not limited to, natural or synthetic elastomers, such as polyisobutylene, styrene, butadiene, styrene isoprene block copolymers, acrylics, urethanes, silicones, styrene butadiene copolymers, methyl acrylate copolymers, acrylic acid, and the like, polyacrylates including, but not limited to, polyacrylic acid polymers lightly crosslinked with a polyalkenyl polyether such as those commercially available from B.F. Goodrich, Cincinnati, Ohio, under the trademarks CARBOPOL 934, 934P, 940 and 941 and the like, poloxamers and natural and synthetic polysaccharides (carbohydrates hydrolysable into two or more molecules of monosaccharides or their derivatives) and polysaccharide gums such as, karaya gum, tragacanth gum, pectin, guar gum, ghatti gum, xanthan gum, jaraya gum and the like, gums such as guar gum, locust bean gum, psillium seed gum and the like, cellulose, and cellulose derivatives such as hydroxyethylcellulose, carboxymethylcellulose, methylcellulose, propylcellulose, cellulose acetate, and the like, mixtures of sulfated sucrose and aluminum hydroxide, substances known for use in transdermal preparations capable of forming a solid colloid that can adhere to mucosa or teeth, used alone or in combination with other suitable carriers and edible additives, such as binders, stabilizers, preservatives, flavorings and pigments.

Multi-layer/multi-zone coated or uncoated films may be used. Multi-zone coating is advantageous for the enclosure of multiple incompatible ingredients, or ingredients which are designed to diffuse in two different directions, such as towards the mucosa to which the film or patch adheres and towards the oral cavity. In addition to the hypodermis-targeted active materials, the transorally-delivered bioadhesive compositions of the present invention may contain additional materials including, but not limited to antimicrobial, teeth-whitening, anti-periodontitis, anti-halitosis, ulcer-healing and sialogogic materials, such as essential oils, metronidazole, zinc oxide, xylitol, glucose oxidase, lysozyme, and lactoferrin, in addition to buffering agents, and artificial flavors and colorings. Thin Film Converting and Platen Sealing technology may be used for converting edible films into oral strips. Brand names include, but are not limited to Thinsol, ARx, and PharFilm.

The carrier for the orally-applied bioadhesive compositions of the present invention is preferably safe for ingestion, biodegradable, controlled-release bioadhesive patch or thin film (which can be also referred to as "oral strip"), having dimensions of about 1 cm by about 3 cm for intraoral application. Such application is preferably to the intraoral mucosa of the parafiltrum or cheeks, or below the lower lip circumferential vermilion-skin border, or to buccal side of the gums or teeth. In a preferred embodiment—for a non-instantaneous effect—the application is effected at or prior to bedtime. In another preferred embodiment—for an instantaneous effect—the application is effected one hour prior to the intended outcome. One or more such strips can be placed simultaneously in the mouth, as desired.

Other oral vehicles for the transorally-delivered bioadhesive compositions of the present invention include, but are not limited to bioadhesive powders, microparticles, or microspheres, and pastes. Cosmetic actives can for example be bound to bioadhesive powders, such as gum-based powders, or be encapsulated in bioadhesive microparticles, liposomes, nanoparticles, nanospheres or microspheres. Such particles may contain surfactants such as a cationic or anionic surfactant which may be entrapped and affixed to the particle surface. Without being bound by scientific theory, it is believed that the bioadhesive properties of the microparticles may be due to the charged surfactants on the particle surface as the hydrophobic ends of the surfactants are embedded in the solid core and the hydrophilic ends are exposed on the surface of the microparticles.

Another suitable method to deliver cosmetic actives to the hypodermis for wrinkle reduction, skin smoothening or facial compartment augmentation is through formulation in emulsions. Any suitable emulsion or microemulsion system may be used, but the emulsion is preferably an oil-in-water or water-in-oil emulsion, wherein the cosmetic compound is dissolved in either the oil phase or the water phase, or can be distributed between the hydrophobic and hydrophilic phases, depending on its physicochemical properties. Surfactant molecules may form various macro-molecular structures in an emulsion, such as micelles, inverse micelles, lipid bilayers (liposomes) and cubosomes, and can be rendered bioadhesives through inclusion of a mucoadhesive proteinous component, such as gelatin. Mucoadhesive proteins can be screened for their ability to be used as mucoadhesives for mucosal delivery of compositions provided herein according to the methodology described in, for example, U.S. Pat. No. 7,906,140. The methodology involves estimating values of adhesive strength between the mucoadhesive protein and the mucous membrane. Advantages of using liposomes as a carrier/encapsulation system is that they are stable and can protect the active agents from degradation, e.g., by oxygen, digestive enzymes, etc.

Mucoadhesive pastes or fluid gels may be for example poloxamer, sodium polyacrylate or polysiloxane-based. To adjust the properties of the base, the paste-like base of the present invention may contain other components, including, but not limited to fatty bases and other auxiliary agents.

Examples of suitable fatty bases include petroleum jelly, paraffins, Plastibase 50W, (which is a mixture of 100 parts by weight of liquid paraffin and 5 parts by weight of a polyethylene of molecular weight 21,000), polyethylene glycol, vegetable fats and oils, waxes, unguentum simplex, hydrophilic vaseline, purified lanolin, dextrin fatty acid esters, fatty acid glycerides, squalane, lanolin alcohol and the like. From about 1 to about 70% by weight and preferably from about 5 to about 50% by weight of these paste adjusting components based on the weight of the base in combination with a bioadhesive agent may be used. Suitable bioadhesive materials include, but are not limited to, carboxylic acid-containing polymers such as copolymers of acrylic or methacrylic acid and the like; esterified polyacrylic acid polymers, such as polyacrylic acid polymers lightly crosslinked with a polyalkenyl polyethers (commercially available from B.F. Goodrich, Cincinnati, Ohio, under the trademarks CARBOPOL® 934, 934P, 974, 940 and 941) and the like; other carbomers, maleic acid copolymers; polysaccharides such as karaya gum, tragacanth gum, xanthan gum, jaraya gum, pectin, guar gum, locust bean gum, psyllium seed gum, alginates and the like, hydrocolloid gels, such as prepared from polysaccharides extracted from Fronia elephantum, Sapindus trifoliatus, Lycium barbarum fruit, Amorphophallus konjac root, the cashew tree and the like; cellulose and cellulose derivatives such as carboxymethyl cellulose, hydroxypropyl cellulose and the like, including mixtures thereof, and mixtures of sulfated sucrose and aluminum hydroxide, along with other substances known for use in transdermal preparations capable of forming a solid colloid that can adhere to tissue, used alone or in combination with other suitable carriers.

To bring about the dissolution of the orally-applied bioadhesive compositions of the present invention at a desired rate in saliva, while releasing the hypodermis-targeted cosmetic active, the bioadhesive compositions may comprise a slowly-dissolving hydrocolloid with a binder that dissolves at a controlled rate in saliva. Suitable binders include, but are not limited to carrageenan (preferably kappa), xanthan gum combined with konjac gum, cellulose fiber, agar and the like. Additional suitable gums include gum arabic, locust bean gum (which has properties similar to konjac gum), and guar gum.

To modulate the adhesiveness of the patch and improve its bioactive properties, the transorally-delivered bioadhesive compositions of the present invention may contain collagen, either in the form of gelatin or a non-denatured form, and the like.

In order to control the pH of the transorally-delivered bioadhesive compositions of the present invention and the pH-sensitive release of hypodermis-targeted cosmetic actives from this system, buffering agents may be used. Preferred buffering compounds include, but are not limited to disodium hydrogen phosphate, calcium chloride, citric acid, sodium citrate, potassium citrate, sodium acetate, ethanolamine, or a combination thereof. Other suitable buffering compounds include acids, such as fumaric acid, tartaric acid, malic acid, adipic acid, and other edible acids or their pharmaceutically acceptable salts. The preferred carbonate salts are sodium carbonate and sodium bicarbonate, however, carbonates and bicarbonates of potassium, ammonium, magnesium, and calcium can also be used.

Lubricants and surfactants may be incorporated in the transorally-delivered bioadhesive compositions of the present invention to enhance performance, for example by improving the compression characteristics of the mixture without changing the release profile or reducing mucoadhesion characteristics (U.S. Pat. No. 5,571,533). Lipid and non-lipid lubricants may be used. Lubricants should be food-grade materials. Suitable non-lipid lubricants may be mucoadhesive or not, and include, but are not limited to, hydrogels, such as CARBOPOL®, water soluble polymers such as polyethylene glycol (molecular weight from 400-1,000,000), glycerol, polypropylene glycol, polyvinyl alcohol, polyvinyl pyrrolidone such as PVP K-30 or PVP K-90, sodium benzoate, leucine, magnesium stearate, sodium lauryl sulfate, and sodium lauryl sulfoacetate and the like. The concentration of the lubricant is from about 0.1% (wt/wt) to about 60% (wt/wt), preferably about 1%.

In certain embodiments, the transorally-delivered bioadhesive compositions of the present invention may contain one or more lipids. The amount of lipid used should be effective to reduce friction and lubricate the mouth following administration of the composition to the subject, particularly if the subject is a xerostomia patient, as well as to generally enhance the transfer of the cosmetic materials from the bioadhesive delivery vehicle to the oral mucosa. Suitable lipids include fatty-acids and their derivatives (including tri-, di-, and monoglycerides and phospholipids) and the like, fatty alcohols and their derivatives, as well as other fat-soluble sterol-containing metabolites such as cholesterol and the like. In another embodiment, the lipid lubricant is a triglyceride, including, but not limited to, tricaprin, trilaurin, triacetin, trimpistin, and triolein and the like. In another embodiment, the lipid lubricant is a phospholipid, including, but not limited to, a phosphoglyceride (e.g., phosphatidyl serine, phosphatidyl inositol, phosphatidyl ethanolamine, and phosphatidyl choline), sphingomyelin and the like. Lecithin from soybeans or other plant source is also a suitable lipid lubricant. Suitable lipids may be in the form of liposomes. Preferred lipids are generally those that melt at or around body temperature so that they are solid at room temperature, but become semiliquid or liquid at the body temperature. Examples of preferred lipids include, but are not limited to, tricaprin, ethyl stearate, short chain waxes, partially hydrogenated plant oils such as olive, grapeseed, jujube, lycium berbarum, canola or corn oil and the like. Additional preferred lipids include mono-, di-, and triglycerides and mixtures thereof, semisolid phospholipids and hydrophobic short chain polymers, such as polycaprolactone.

The concentration of the lipid lubricant in the transorally-delivered bioadhesive compositions of the present invention is preferably from about 7.5% to about 50% by weight of the composition.

The concentration of all bioadhesive components in the patch can vary between 1% and 99%, the remaining part being provided by the hypodermis-targeted cosmetic agents, surfactants and/or fillers.

The transorally-delivered bioadhesive compositions of the present invention may be applied by finger, by spray, by an applicator such as a syringe, be placed by tweezers, or by any other suitable method. The compositions may also be applied in the form of a chewing gum.

The above-mentioned systems can be used in combination with any suitable topical cosmetic product in order to achieve additional skin protection.

DETAILED DESCRIPTION OF PREFERRED EMBODIMENTS

The following examples illustrate various embodiments of the present invention. They are not to be construed to limit the invention to any of the specific details described therein.

EXAMPLE 1

A biodegradable, bioadhesive thin patch was prepared by mixing gelatin, carboxymethylcellulose, purslane leaf extract (standardized to 5% flavones), grape seed extract, lecithin and magnesium ascorbyl phosphate in water, in order to obtain a product containing 45% of gelatin, 39.5% of carboxymethylcellulose, 2.5% grape seed extract, 7.5% lecithin, 5% purslane extract and 0.5% magnesium ascorbyl phosphate afterward the mixture was spread as a 0.3 mm-thin film on a non-porous surface, until dry.

EXAMPLE 2

The patch from EXAMPLE 1 was cut in 6 mm×40 mm rectangles and applied daily at bedtime to the oral mucosa of parafiltrum. After 15 days, a visible reduction of perioral wrinkles was observed, along with a smoother, plumped lip effect.

EXAMPLE 3

The patch from EXAMPLE 1 supplemented with 20% pectin is cut in 10 mm×20 mm rectangles and applied daily at bedtime to the oral mucosa in the vicinity of cheek fat pads. After 30 days, a visible reduction of smile lines and nasolabial folds was observed.

EXAMPLE 4

The patch from EXAMPLE 1 was cut in 6 mm×40 mm rectangles and applied daily at bedtime intraorally on the mucosa of the oral side of the parafiltrum. After 5 days, vertical relaxation of the parafiltrum was observed resulting in the better coverage of gums during smiling and in the reduction of the "gummy smile" appearance by 4 mm.

EXAMPLE 5

Full-thickness human skin explants were contacted at the hypodermal level with DMEM-type medium containing 100 micrograms/ml of (1:3) mixture of grape seed extract and lecithin (named SBD.5AC). The control explants were contacted with same medium without the grape seed extract/lecithin mixture. After 48 hours incubation skin was defatted, tissues are disrupted with a homogenator, total RNA is extracted and compared for the expression of 86 genes coding for adhesion and extracellular matrix proteins using PCR arrays (Qiagen, cat. #PAHS-013A). The results (Table I) show that contacting the deepest layer of the skin—hypodermis with SBD.5AC was sufficient to trigger a desirable modulation of gene expression responsible for the strengthening of the dermal-epidermal junction (increase of LAMB3 and TNC expression) in the upper layers of the skin, and to cause an overall favorable modulation of genes coding for extracellular matrix components (COL1A1) and ECM-digesting metalloproteinases (MMP1, MMP3 and MMP8), when gene expression was standardized to housekeeping genes. SBD.5AC also upregulated an elastin-digesting protease MMP-12, however it also inhibited the enzymatic activity of elastase (Table II) so that the overall effect of SBD.5AC on elastin-digesting enzymes in vivo may still be inhibitory.

This example demonstrates that the application in vitro of skin-active materials to the lowest layer of the skin—the hypodermis, is sufficient for obtaining a measurable beneficial effect on the gene expression in the upper layers of the skin—dermis and epidermis.

TABLE I

Fold change of gene expression in human skin explants treated with SBD.5AC at hypodermis-level, as compared with water-treated control explants.

| Gene Name | Fold regulation |
| --- | --- |
| COL1A1 | 2.8 |
| ECM1 | −3.5 |
| LAMB3 | 4.9 |
| MMP1 | −2.3 |
| MMP12 | 2.8 |
| MMP3 | −2.1 |
| MMP8 | −2.1 |
| TNC | 4.6 |

TABLE II

SBD.5AC exhibits statistically-significant and dose-dependent inhibition of elastase enzymatic activity, in vitro.

| Test Material | Elastase Activity (% Ctr) | p value (two tailed Student t-test) |
| --- | --- | --- |
| H2O | 100 | 1 |
| SBD.5AC 20 µg/ml | 57 | 0.000 |
| SBD.5AC 100 µg/ml | 48 | 0.002 |

EXAMPLE 6

Full-thickness human skin explants were contacted at the hypodermal level with DMEM-type medium containing 100 micrograms/ml of (1:3) mixture of grape seed extract and lecithin (working name: SBD.5AC). The control explants were contacted with same medium without the grape seed extract/lecithin mixture. After 5 days incubation, tissues were formalin fixed, sectioned and stained with hematoxylin/eosin (H&E). The microscopic evaluation under ×40 and ×200 magnification shows thicker, better preserved and more uniform epiderm in skin explants cultured in medium supplemented with SBD.5AC as compared with the water-treated control samples.

This example demonstrates that the application in vitro of skin-active materials to the lowest layer of the skin—the hypodermis, is sufficient for obtaining improvement of morphologic appearance at the upper layers of the skin—dermis and epidermis.

EXAMPLE 7

This is an example of a transoral delivery formulation with starch microspheres containing magnesium creatine complex and linseed extract for wrinkle reduction and cheek plumping.

15 ml of 5% starch solution (pH=7) is mixed with 0.1 g of magnesium creatine and 1 g of *Centella asiatica* extract and stirred at constant temperature of 37° C. and stirred (500 rpm) while a 30% solution of polyethylene glycol (PEG 4000) is added (about 7 ml) until phase separation occurs. The system is then stirred for a further 15 min, before it is cooled on ice during constant stirring. The microspheres are then isolated by filtration and freeze dried. With a stirring speed of 500 rpm, particles with a mean size of 33 µm±10 µm are produced. Particles are applied by spray applicator on the buccal side of the lips and cheeks.

EXAMPLE 8

Peppermint-Flavored Ointment with Niacin for Lip Augmentation

A 2% niacin ointment is prepared by adding 10 grams of niacin and 0.1 ml of peppermint oil to 99.9 ml of propylene glycol (1,2-propanediol) at room temperature under stirring. This liquid niacin suspension is then progressively admixed in batches with 400 grams of commercial Aquaphor™ ointment (produced by Beiersdorf Inc. a German Company with U.S. offices in Wilton, Conn.) to obtain the ointment, which is stored in standard 1 oz. vials and applied on the lip and above and below the vermillion border of the oral mucosa for lip augmentation effect.

EXAMPLE 9

Formulation for extracellular matrix enhancement with transoral delivery of banaba leaf extract whey protein hydrolysate and proline (using the delivery platform disclosed in U.S. Published Application Serial No. 2010/0080829).

Components: Whey protein hydrolysate: 20 mg; Proline: 20 mg; Banaba leaf extract 10 mg; Gelling agent Poloxamer 407 15 mg; Bioadhesive methylcellulose polymer (Methocel® A 15): 10 mg; Binder Dextran 70 10 mg; Filler mannitol 115 mg; Purified water 235 mg.

Preparation: The bioadhesive methylcellulose polymer (Methocel® A 15) is dissolved in water at 60-70° C., and the gelling agent, Poloxamer 407 is dissolved in water at 10-20° C. in separate containers. Then a viscous water suspension containing the both the bioadhesive polymer and the gelling agent is prepared by mixing an aqueous solution containing Methocel® A 15 and an aqueous solution containing Poloxamer 407 at 15-25° C. Then, the remaining ingredients, which are whey protein hydrolysate, proline, binder (Dextran 70) and filler (mannitol) are introduced to the viscous solution at 15-25° C. The suspension is mixed until it is substantially homogeneous, then deposited into preformed blisters, frozen and lyophilized.

EXAMPLE 10

Transoral formulation with retinol, *Centella asiatica* extract and Acacia acinacea extract for wrinkle reduction.

Na-alginate polymer mixtures are prepared using a magnetic stirrer to which 0.3% glycerine is added as a plasticizer, followed by the addition of 0.2% retinol (50% in polysorbate 20), 5% *Centella asiatica* (20% water extract), 5% Acanesia acinacea (20% water extract). The resulting solution is poured in a glass mold and the film is dried at room temperature for 48 hours. The film is cut in 1 cm×3 cm rectangles and applied on the buccal side of the upper and lower lip, as well as on the buccal side of cheeks for wrinkle reduction.

The present invention is not to be limited in scope by the specific descriptions above, which are intended as illustrations of a few aspects of the invention that are within the scope of this invention. Indeed, various modifications of the invention in addition to those shown and described herein will become apparent to those skilled in the art and are intended to fall within the scope of the appended claims.

We claim:

1. A bioadhesive patch consisting essentially of a *Portulaca oleracea* leaf extract, magnesium ascorbyl phosphate.

2. The bioadhesive patch of claim 1, Wherein the patch is a slow release patch.

3. The bioadhesive patch of claim 1, wherein said *Portulaca oleracea* leaf extract is in an amount of about 1% to about 35% by weight and said magnesium ascorbyl phosphate is in an amount of about 0.1% to about 10% by weight.

4. A bioadhesive patch consisting essentially of a *Portulaca oleracea* leaf extract, GABA, grape seed extract, carboxymethylcellulose, collagen, and magnesium ascorbyl phosphate.

5. The bioadhesive patch of claim 4, wherein the patch is a slow release patch.

6. The bioadhesive patch of claim 4, wherein said *Portulaca oleracea* leaf extract is in an amount of about 1% to about 35% by weight, said magnesium ascorbyl phosphate is in an amount of about 0.1% to about 10% by weight, and said grape seed extract is in an amount of about 1% to about 35% by weight.

7. The bioadhesive patch of claim 4, wherein said *Portulaca oleracea* leaf extract is in an amount of about 1% to about 35% by weight, said magnesium ascorbyl phosphate is in an amount of about 0.1% to about 10% by weight, said grape seed extract is in an amount of about 2.5% by weight, and said carboxymethylcellulose is in an amount of about 39.5% by weight.

8. A bioadhesive patch consisting essentially of a *Portulaca oleracea* leaf extract, GABA, grape seed extract, carboxymethylcellulose, collagen, and, magnesium ascorbyl phosphate; wherein said collagen is selected from gelatin form, non-denatured form, or a combination thereof.

9. The bioadhesive patch of claim 8, wherein said collagen is in an amount of about 45% by weight.

10. A bioadhesive patch consisting essentially of a *Portulaca oleracea* leaf extract, grape seed extract, carboxymethylcellulose, collagen, and magnesium ascorbyl phosphate.

11. The bioadhesive patch of claim 10, wherein the patch is a slow release patch.

12. The bioadhesive patch of claim 10, wherein said *Portulaca oleracea* leaf extract is in an amount of about 1% to about 35% by weight, said magnesium ascorbyl phosphate is in an amount of about 0.1% to about 10% by weight, and said grape seed extract is in an amount of about 1% to about 35% by weight.

13. The bioadhesive patch of claim 10, wherein said *Portulaca oleracea* leaf extract is in an amount of about 5% by weight, said magnesium ascorbyl phosphate is in an amount of about 0.5% by weight, said grape seed extract is in an amount of about 2.5% by weight, and said carboxymethylcellulose is in an amount of about 39.5%.

14. The bioadhesive patch of claim 10, wherein said collagen is in a form selected from gelatin form, non-denatured form, or a combination thereof.

15. The bioadhesive patch of claim 10, wherein said collagen is in an amount of about 45% by weight.

16. A bioadhesive patch consisting essentially of a *Portulaca oleracea* leaf extract, GABA, grape seed extract, carboxymethylcellulose, and magnesium ascorbyl phosphate.

17. The bioadhesive patch of claim 16, wherein the patch is a slow release patch.

18. The bioadhesive patch of claim 16, wherein said *Portulaca oleracea* leaf extract is in an amount of about 1% to about 35% by weight, said magnesium ascorbyl phosphate is in an amount of about 0.1% to about 10%, and said grape seed extract is in an amount of about 1% to about 35% by weight.

19. The bioadhesive patch of claim 16, wherein said *Portulaca oleracea* leaf extract is in an amount of about 5%, said magnesium ascorbyl phosphate is in an amount of about 0.5%, said grape seed extract is in an amount of about 2.5%, and said carboxymethylcellulose is in an amount of about 39.5%.

* * * * *